(12) United States Patent
Schleper et al.

(10) Patent No.: US 8,679,829 B2
(45) Date of Patent: Mar. 25, 2014

(54) ARCHAEON EXPRESSION SYSTEM

(75) Inventors: Christa Schleper, Klosterneuburg (AT); Melanie Jonuscheit, Darmstadt (DE); Jürgen Eck, Bensheim (DE); Frank Niehaus, Heppenheim (DE); Sonja-Verena Albers, ST Groningen (DE); Sabrina Froels, Dreieich (DE)

(73) Assignee: B.R.A.I.N. Biotechnology Research and Information Network AG (DE)

( * ) Notice: Subject to any disclaimer, the term of this patent is extended or adjusted under 35 U.S.C. 154(b) by 1715 days.

(21) Appl. No.: 10/559,583

(22) PCT Filed: Jun. 2, 2004

(86) PCT No.: PCT/EP2004/005936
§ 371 (c)(1),
(2), (4) Date: May 10, 2006

(87) PCT Pub. No.: WO2004/106527
PCT Pub. Date: Dec. 9, 2004

(65) Prior Publication Data
US 2007/0134201 A1    Jun. 14, 2007

(30) Foreign Application Priority Data
Jun. 2, 2003    (EP) .................................... 03012552

(51) Int. Cl.
| C12N 15/00 | (2006.01) |
| C12N 15/866 | (2006.01) |
| C12N 15/70 | (2006.01) |
| C12N 15/11 | (2006.01) |

(52) U.S. Cl.
USPC ................... 435/320.1; 424/93.2; 424/199.1; 536/23.1; 536/24.1

(58) Field of Classification Search
None
See application file for complete search history.

(56) References Cited

U.S. PATENT DOCUMENTS 6,927,026 B1 * 8/2005 Pompejus et al. ........... 435/6.18

OTHER PUBLICATIONS

Ciaramella, M., et al., Molecular biology of extremophiles: recent progress on the hyperthermophilic archaeon Sulfolobus, Antonie van Leeuwenhoek, 81:85-97 (2002).
Jonuscheit, M., et al., A reporter gene system for the hyperthermophilic archeon Sulfolobus solifataricus based on a selectable and integrative shuttle vector, Molecular Microbiology, 48(5):1241-1252 (2003).
Stedman, K.M., et al., Genetic requirements for the function of the archaeal virus SSV1 in Sulfolobus solfataricus: Construction and testing of viral shuttle vectors, Genetics, 152:1397-1405 (1999).
Stedman, K.M., et al., Extremophile genetics, Second Astrobiology Science Conference, Apr. 7, 2002 (Internet abstract).
Stedman, K.M., et al., Relationships between fuselloviruses infecting the extremely thermophilic archaeon Sulfolobus: SSV1 and SSV2, Research in Microbiology, 154:295-302 (2003).

* cited by examiner

Primary Examiner — Maria Marvich
(74) Attorney, Agent, or Firm — Pillsbury Winthrop Shaw Pittman LLP

(57) ABSTRACT

The present invention relates to a sulfolobus expression vector comprising: (a) sulfolobus origin of replication; (b) the genes encoding the structural proteins and the site-specific integrase of SSV1, SSV2 or pSSVx, operatively linked to expression control sequences and a packaging signal; (c) one or more selectable marker gene(s), operatively linked to sulfolobus expression control sequences; and (d) a sulfolobus promoter followed 3' by a restriction enzyme recognition site or a multiple cloning site for insertion of a gene of interest and optionally a 3' regulatory element. Moreover, the present invention relates to a shuttle vector comprising the sequences of the expression vector of the invention and additional sequences for propagation and selection in E. coli, wherein the additional sequences comprise (a) an E. coli on of replication; and (b) a marker for selection in E. coli. Furthermore, the invention relates to host cells transformed with the expression vector as well as to a kit comprising a vector or a host cell of the present invention. Finally, the present application also relates to a method for generating infectious subviral particles.

19 Claims, 16 Drawing Sheets

Figure 2:
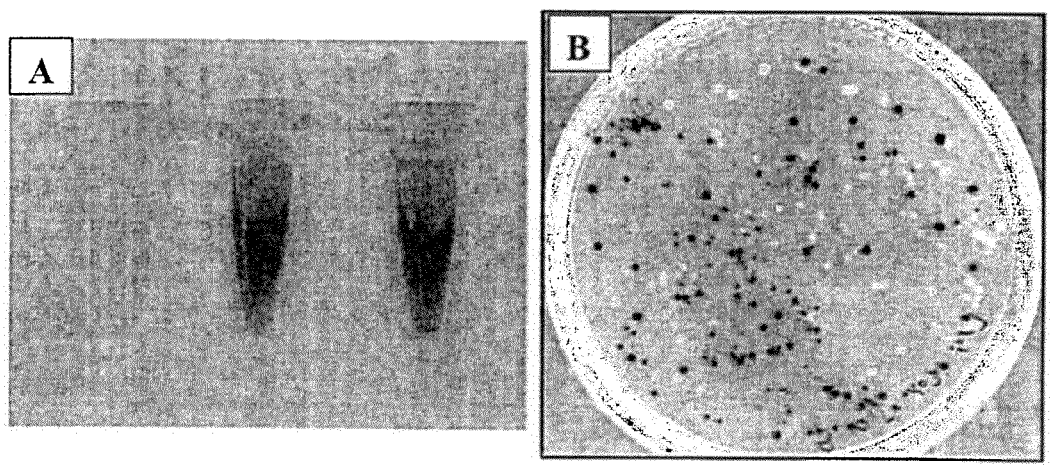

Figure 1
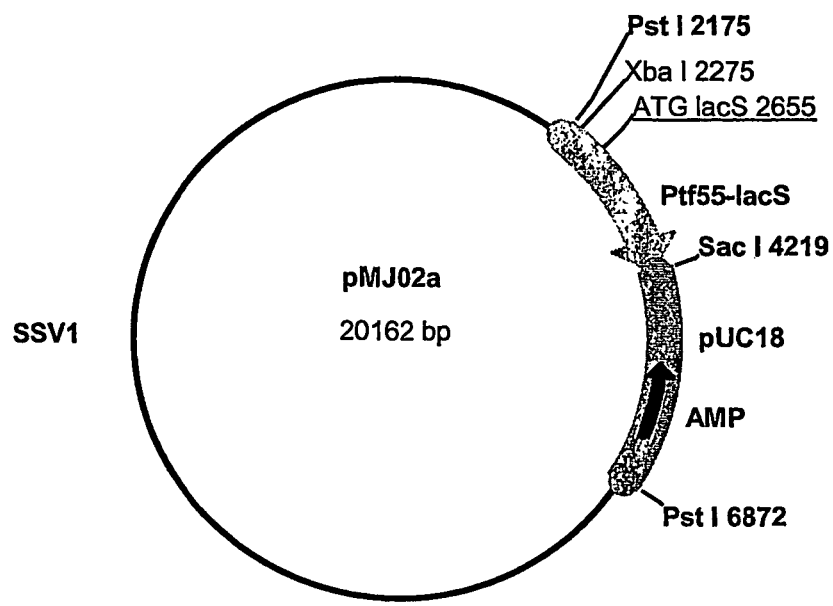
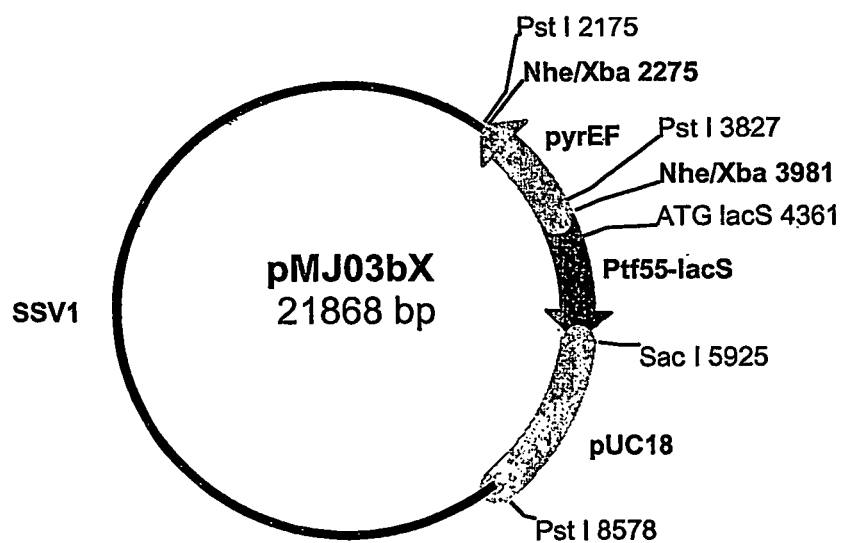

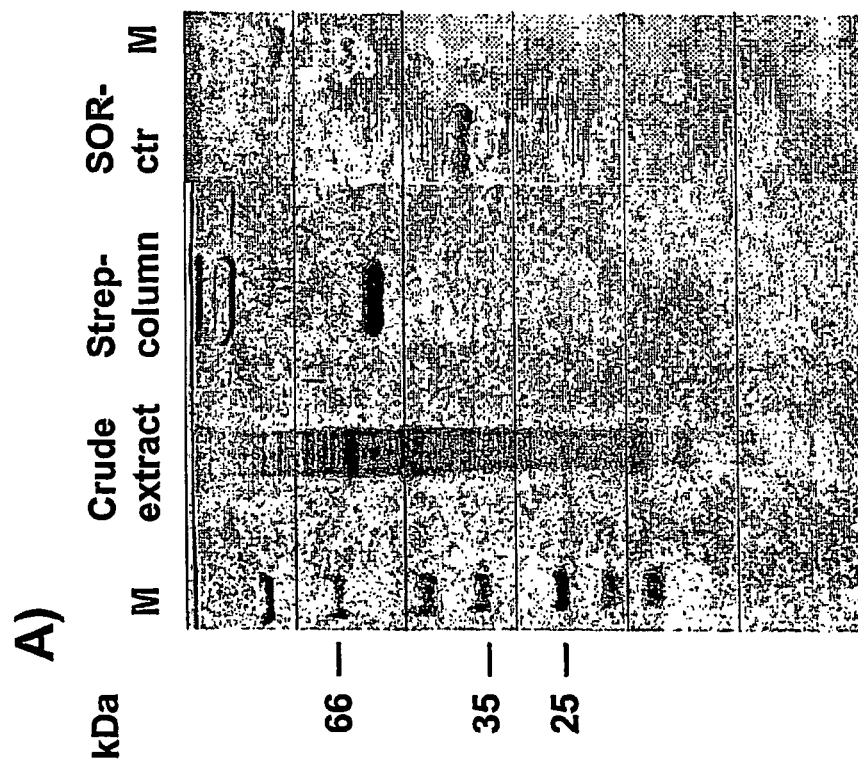
Fig 8b: A) SDS-PAGE of sor purification
B) Activity plot oxygenase/reductase

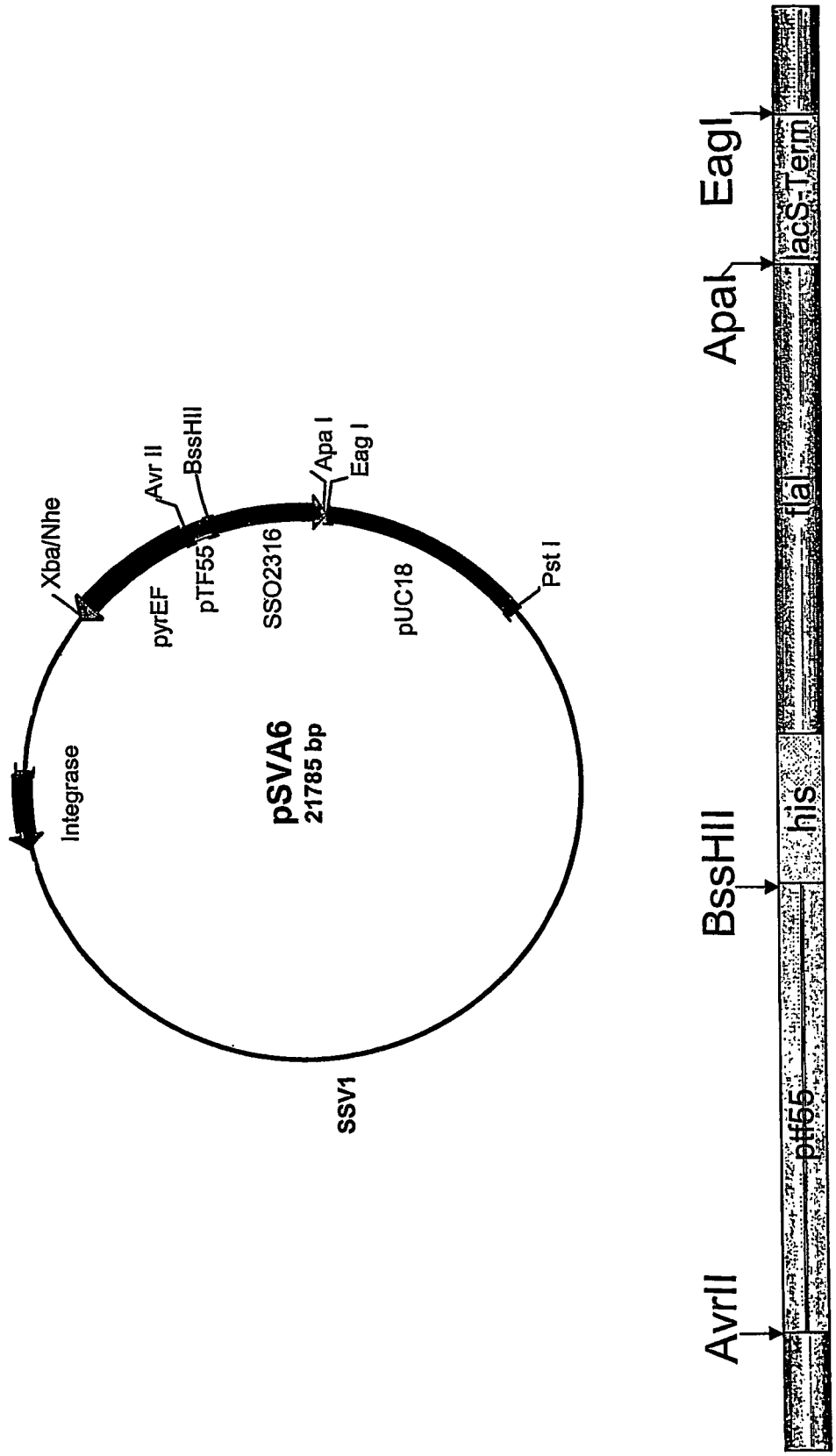
Fig. 9: E.coli / Sulfolobus shuttle vector pSVA6

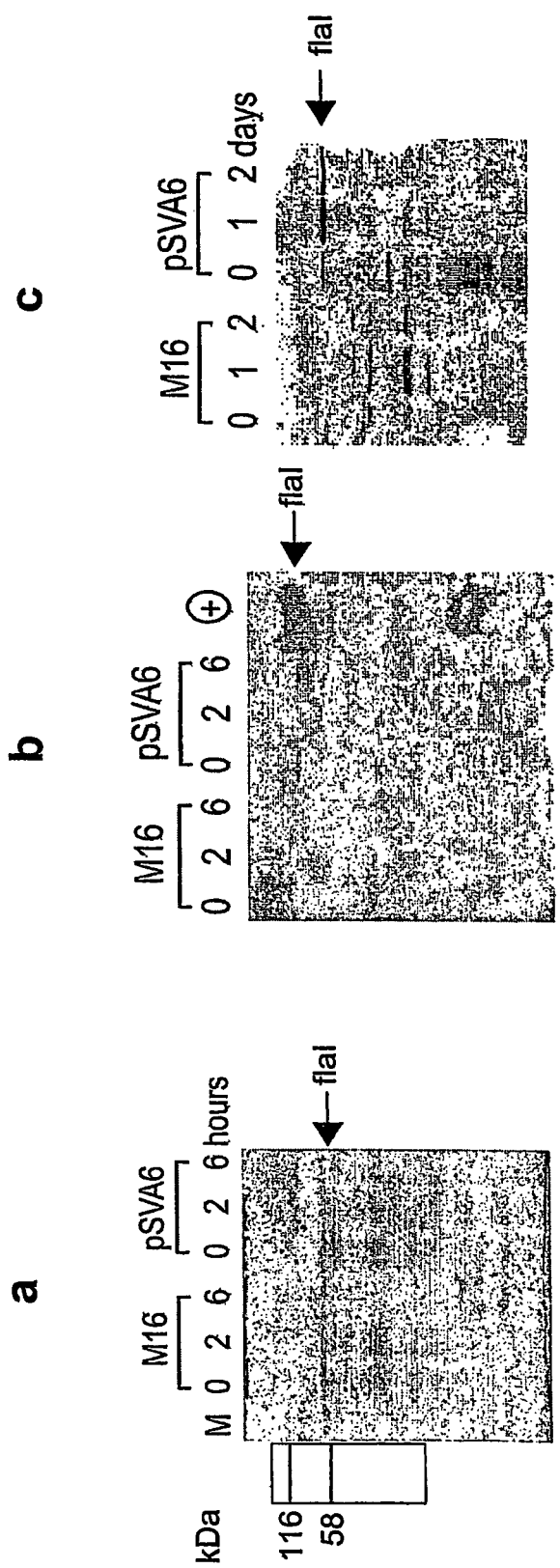
Fig. 10: Expression of flaI and western blot analysis

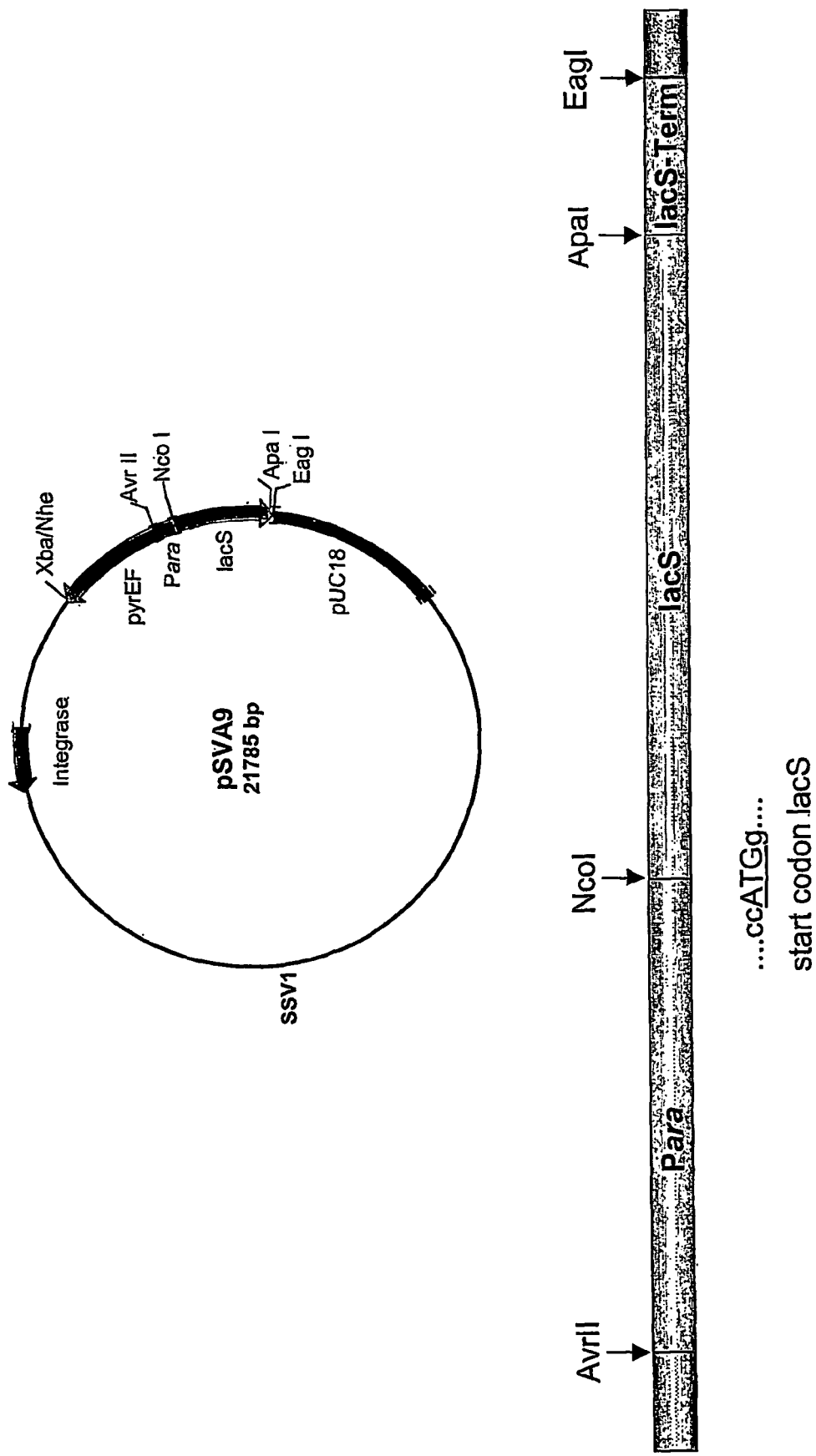
Fig. 11: Expression vector pSVA9 containing the S. solfataricus arabinose promoter

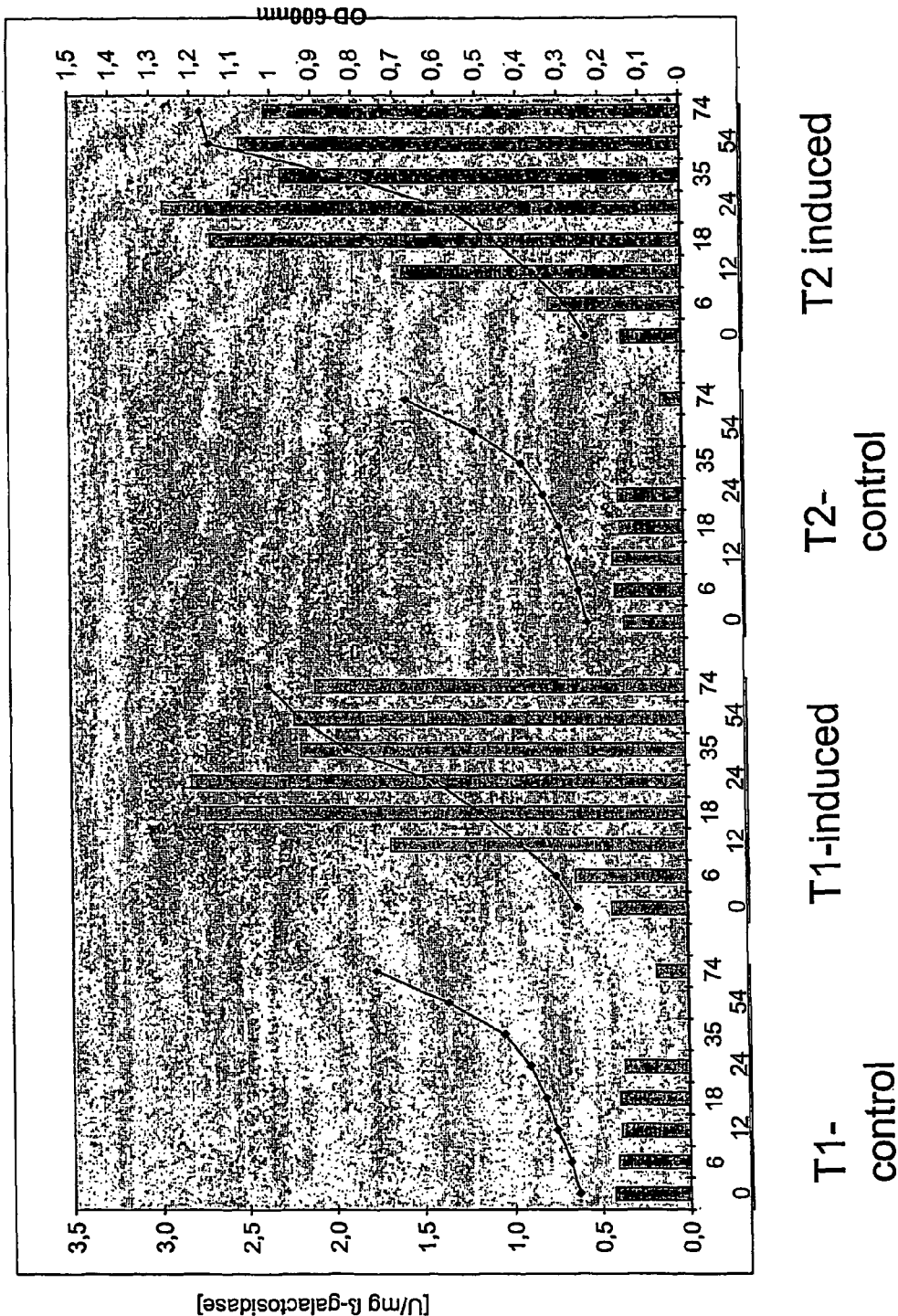
Fig. 12: Activity panel of pSVA9 transformants under induced and non-induced (control-) conditions Figure 13:
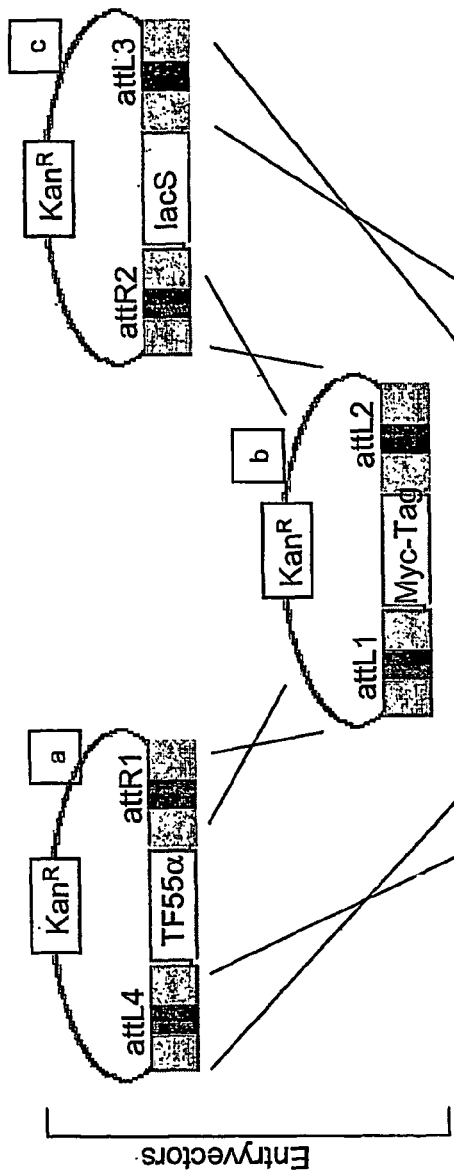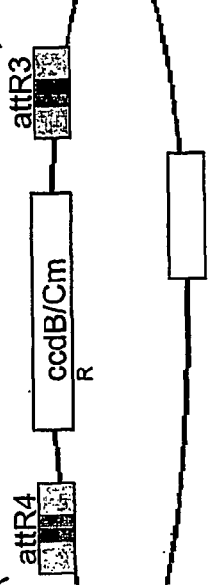

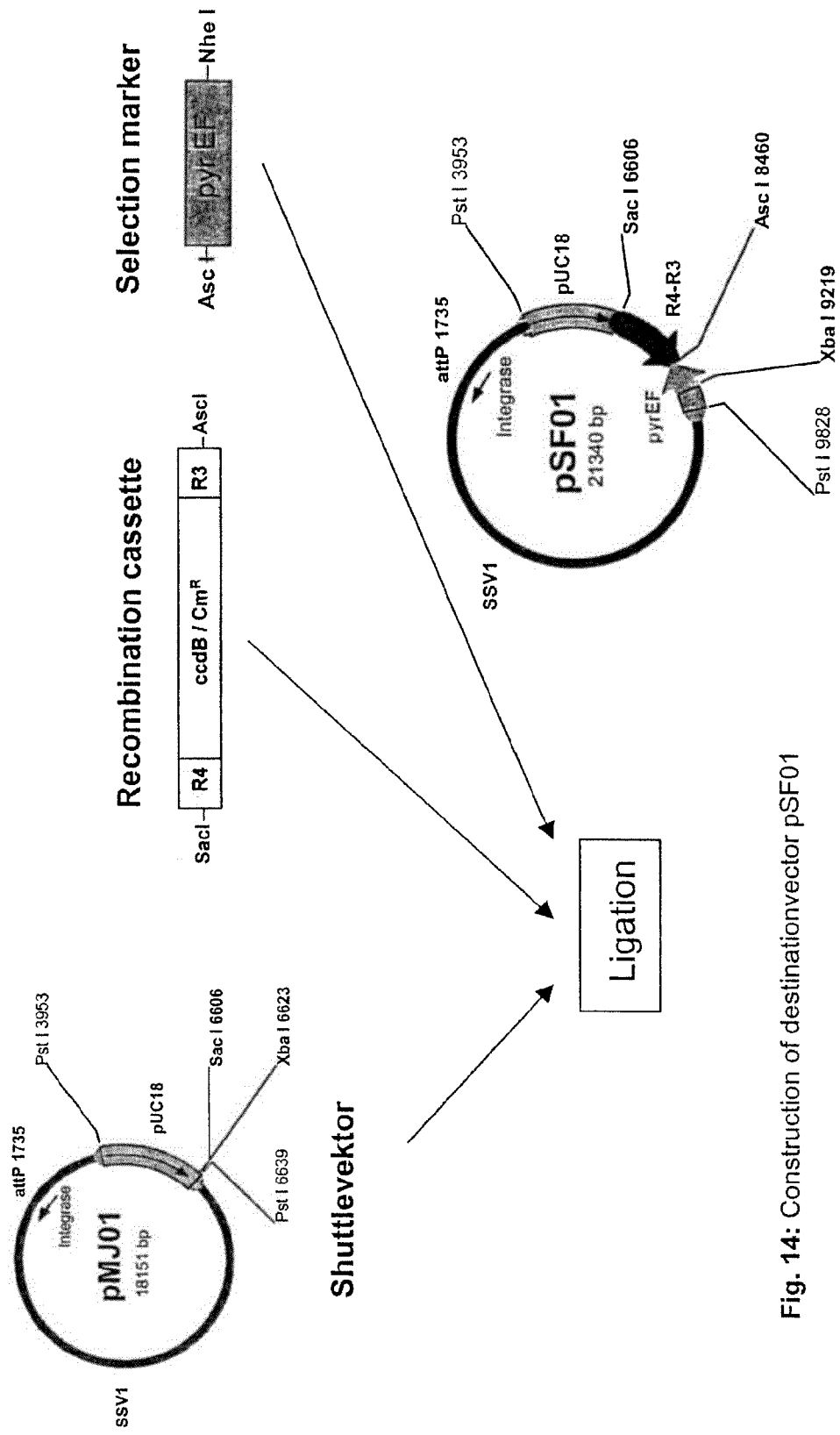
Fig. 14: Construction of destinationvector pSF01

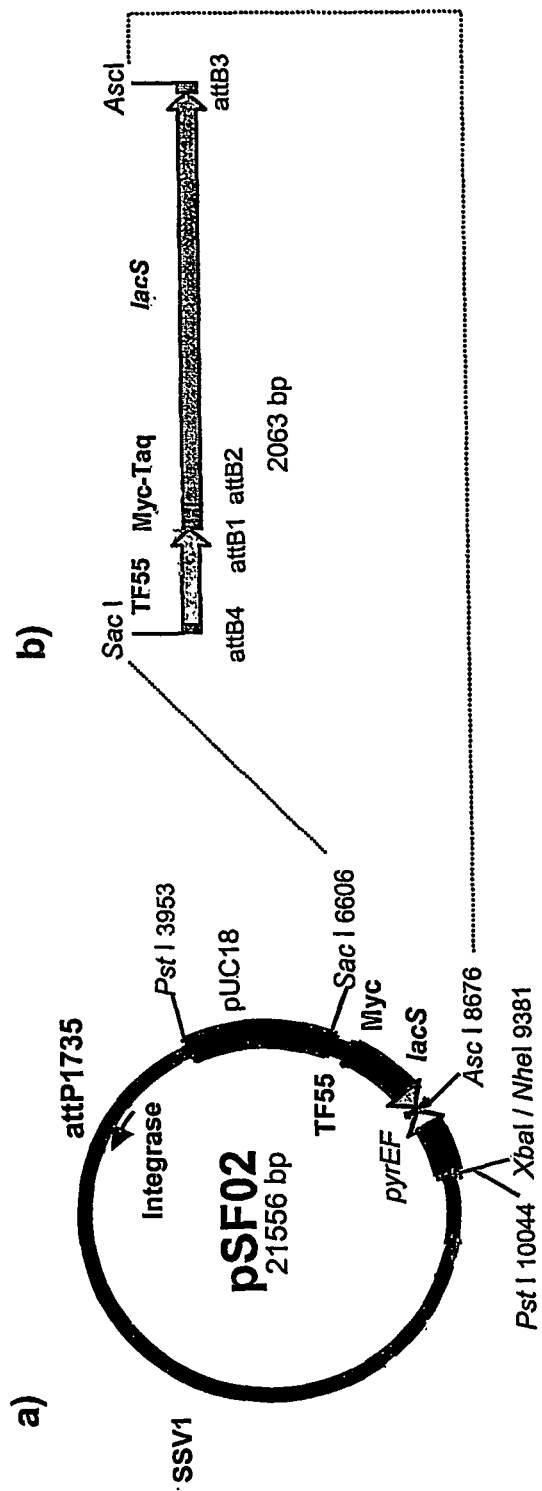
Fig. 15: a) Expression-Shuttlevektor pSF02;
b) detailed drawing of expressioncassette

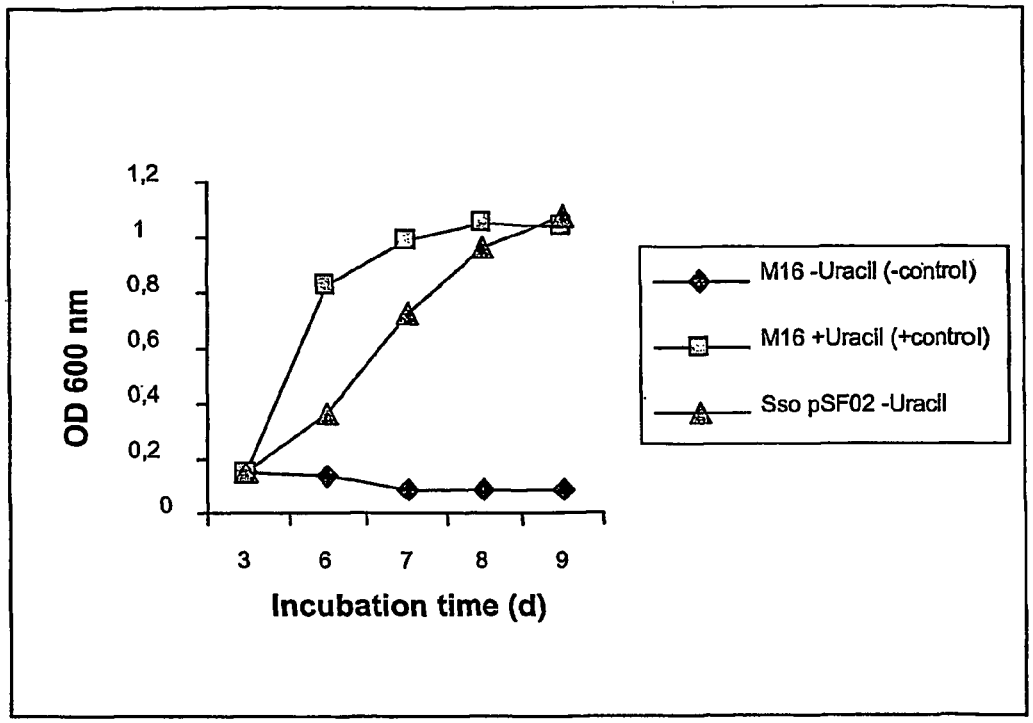
Fig. 16: Growth curve of Sulfolobus solfataricus pSF02 in selection medium (- Uracil)
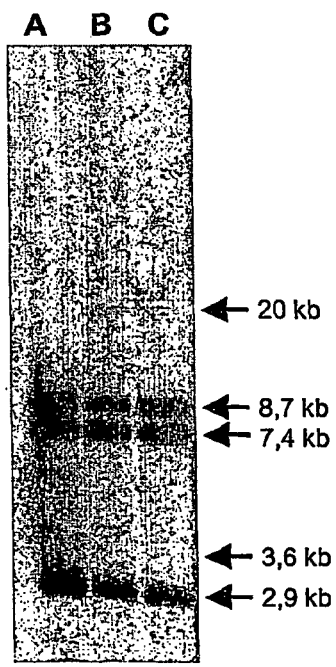
Fig. 17:
Southern-Blot-analysis of S. solfataricus pSF02
A) pSF02 control DNA
B) S. solfataricus pSF02 clone 1 (total DNA)
C) S. solfataricus pSF02 clone 2 (total DNA)

```
                        SEQUENCE LISTING

<160> NUMBER OF SEQ ID NOS: 6

<210> SEQ ID NO 1
<211> LENGTH: 30
<212> TYPE: DNA
<213> ORGANISM: Sulfolobus solfataricus

<400> SEQUENCE: 1
gctccagtca tgtactcatt tccaaatagc                                          30

<210> SEQ ID NO 2
<211> LENGTH: 21
<212> TYPE: DNA
<213> ORGANISM: Sulfolobus solfataricus

<400> SEQUENCE: 2
gaaacggccg gcaatctaat g                                                   21

<210> SEQ ID NO 3
<211> LENGTH: 21
<212> TYPE: DNA
<213> ORGANISM: Sulfolobus solfataricus

<400> SEQUENCE: 3
attaagtcgg ccgtcaagaa a                                                   21

<210> SEQ ID NO 4
<211> LENGTH: 27
<212> TYPE: DNA
<213> ORGANISM: Sulfolobus solfataricus

<400> SEQUENCE: 4
tgagtacatg actggagctg ccatacc                                             27

<210> SEQ ID NO 5
<211> LENGTH: 24
<212> TYPE: DNA
<213> ORGANISM: Sulfolobus solfataricus

<400> SEQUENCE: 5
tctcgctagc gaataatgct gccc                                                24

<210> SEQ ID NO 6
<211> LENGTH: 24
<212> TYPE: DNA
<213> ORGANISM: Sulfolobus solfataricus

<400> SEQUENCE: 6
ttacgctagc ttcctcgtgt agat                                                24
```

ARCHAEON EXPRESSION SYSTEM

The present invention relates to a sulfolobus expression vector comprising: (a) sulfolobus origin of replication; (b) the genes encoding the structural proteins and the site-specific integrase of SSV1, SSV2 or pSSVx, operatively linked to expression control sequences and a packaging signal; (c) one or more selectable marker gene(s), operatively linked to sulfolobus expression control sequences; and (d) a sulfolobus promoter followed 3' by a restriction enzyme recognition site or a multiple cloning site for insertion of a gene of interest and optionally a 3' regulatory element. Moreover, the present invention relates to a shuttle vector comprising the sequences of the expression vector of the invention and additional sequences for propagation and selection in E. coli, wherein the additional sequences comprise (a) an E. coli ori of replication; and (b) a marker for selection in E. coli. Furthermore, the invention relates to host cells transformed with the expression vector as well as to a kit comprising a vector or a host cell of the present invention. Finally, the present application also relates to a method for generating infectious subviral particles.

Several documents are cited throughout the text of this specification. The disclosure content of the documents cited herein (including any manufacture's specifications, instructions, etc.) is herewith incorporated by reference.

Sulfolobus solfataricus is one of the best studied species of hyperthermophilic organisms. It belongs to the Crenarchaeota, one of the two major phyla of the domain archaea which are almost exclusively represented by hyperthermophiles. Despite its extreme growth requirements (temperature optimum of 78° C., pH optimum of 3) Sulfolobus can be relatively easily grown under aerobic and heterotrophic conditions in liquid culture and on plates. Due to its ease of cultivation several pioneering studies on archaeal metabolism have been done with Sulfolobus solfataricus and its relatives (e.g. Bouthier de la Tour et al. 1990, Grogan and Gunsalus 1993, Schafer 1996, Edgell et al. 1997, Elferink et al. 2001, Vitagliano et al. 2001, Wadsworth and White 2001). Furthermore, in vitro studies of transcription, translation and replication in Sulfolobus have provided important insights into the fundamentals of information processing in archaea (Condo et al. 1999, De Felice et al. 1999, Bell et al. 2001, Hjort and Bemander 2001).

With the help of an in vitro transcription system it has been demonstrated, that the basal transcription apparatus of archaea is similar to that of eukaryotes, albeit simpler in composition (reviewed in Bell and Jackson 2001). In brief, the single, rather complex RNA polymerase in archaea, together with a TATA-binding protein (TBP) and TFB, both homologs of the eukaryal transcription factors TBP and TFIIB, respectively, are sufficient to direct accurate initiation of transcription on promoters that contain a TATA-box and BRE element reminiscient of RNA-polymerase II promoters of eukaryotes.

While basic transcription and some regulators have been well studied in vitro, it has not been possible to analyse gene regulation in vivo in hyperthermophiles due to the lack of a powerful genetic system. Efficient genetic systems including reporter genes have only been established for non-thermophilic, halophilic archaea (Patenge et al. 2000, Gregor and Pfeifer 2001). The complete genome sequence of S. solfataricus has been determined (She et al. 2001) and a number of genetic elements, such as viruses, conjugative plasmids and small high-copy-plasmids have been characterized and sequenced (for review see Zillig et al. 1998). These elements have served to develop the first genetic tools for Sulfolobus, including a transformation/transfection procedure and shuffle vectors (Schleper et al. 1992, Schleper et al. 1995, Aagaard et al. 1996, Elferink et al. 1996, Aravalli and Garrett 1997, Cannio et al. 1998). However, none of the systems described so far have been useful for efficient cloning in Sulfolobus, for the high-level expression of proteins or for systematic tests of promoter activities based on a reporter gene. Difficulties were apparently due to low transformation efficiencies, inefficient selection and/or instability of the vectors in the host.

Thus and in of the above, the technical problem underlying the present invention was to provide a genetically stable and highly efficient cloning and expression system for Sulfolobus. The solution to this technical problem is achieved by providing the embodiments characterized in the claims. Accordingly the present invention relates to a sulfolobus expression vector comprising (a) a sulfolobus origin of replication; (b) the genes encoding the structural proteins and the site-specific integrase of SSV1, SSV2 or pSSVx, operatively linked to expression control sequences and a packaging signal; (c) one or more selectable marker gene(s), operatively linked to sulfolobus expression control sequences; and (d) a sulfolobus promoter followed 3' by a restriction enzyme recognition site or a multiple cloning site for insertion of a gene of interest and optionally a 3' regulatory element.

The term "sulfolobus" refers to the hyperthermophilic Archaeon genera Sulfolobus and comprises the species Sulfolobus acidocaldarius, Sulfolobus brierleyi, Sulfolobus hakonensis, Sulfolobus metallicus, Sulfolobus shibatae, Sulfolobus solfataricus. The terms "origin of replication", "ori of replication" or "ori" refer to a region of DNA that is essential for starting its replication.

The terms "site-specific integrase" or "site-specific recombinase" refer to an integrase molecule which is capable of catalysing the integration of DNA into a specific site in the host chromosome. The attachment site for insertion can be located within the coding sequence of the integrase gene of the expression vector as in the case of SSV1 (vide infra) or outside in the remaining nucleotide sequences of the expression vector. Preferably, the integrase is obtainable from the DNA of SSV1 or SSV2, however, any integrase molecule would be comprised by the present invention as long as it catalyses the integration of the expression vector into the chromosomal DNA of the host.

The terms "SSV1" and "SSV2" refer to types 1 and 2 of Sulfolobus shibatae, a circular double stranded DNA virus adapted to Sulfolobus. The term "expression control sequence" refers to elements on the DNA or RNA that control gene expression and therefore include elements such as promoter, enhancer, silencer, transcription factor B recognition element (BRE), Shine Dalgamo sequence, TATA-box, internal ribosomal entry sites (IRES), attachment sites for transcription factors, sequences important for termination of transcription, polyadenylation sites, RNA transporting signals, sequences important for UV-light or heat-shock response causing either gene induction or repression, signal sequences for secretion, splicing signals or nucleotide sequence elements known to be important for intracellular transport, subcellular localization or translation of the RNA. The term "3' regulatory element preferable refers to a polyadenylation sequence. The term "operatively linked" means that a single or a combination of the above-described control elements together with the coding sequence of the gene are capable of directing protein expression from the gene. The term "packaging signal" refers to a region on the viral nucleic genome capable of directing the attached nucleic acid molecules into the envelope of the virion. Although the specific location of the packaging signal is presently unknown, the packaging signal is likely to comprise a region of the DNA capable of interacting with the protein encoded by SSV1 ORF a153 and/or b251 or by the homologous ORF of SSV2. In a particularly preferred embodiment of the present invention, the packaging signal is located within the region encoding SSV1 ORF a153 and/or b251 or with the homologous ORF of SSV2. The term "selectable marker gene" refers to proteins that, when expressed in a host cell, confer a phenotype onto the cell which allows a selection of the cell expressing said selectable marker gene. Generally this may be a protein that confers resistance to an antibiotic such as ampicillin, kanamycin, chloramphenicol, tetracyclin, hygromycin, neomycin or methotrexate. Further examples of antibiotics are Penicillins: Ampicillin HCI, Ampicillin Na, Amoxycillin Na, Carbenicillin disodium, Penicillin G, Cephalosporins,. Cefotaxim Na, Cefalexin HCI, Vancomycin, Cycloserine. Other examples include Bacteriostatic Inhibitors such as: Chloramphenicol, Erythromycin, Lincomycin, Tetracyclin, Spectinomycin sulfate, Clindamycin HCI, Chlortetracycline HCI. Additional examples are proteins that allow selection with Bacteriosidal inhibitors such as those affecting protein synthesis irreversibly causing cell death. Aminoglycosides can be inactivated by enzymes such as NPT II which phosphorylates 3'-OH present on kanamycin, thus inactivating this antibiotic. Some aminoglycoside modifying enzymes acetylate the compound and block their entry in to the cell. Gentamycin, Hygromycin B, Kanamycin, Neomycin, Streptomycin, G418, Tobramycin Nucleic Acid Metabolism Inhibitors, Rifampicin, Mitomycin C, Nalidixic acid, Doxorubicin HCI, 5-Flurouracil, 6-Mercaptopurine, Antimetabolites, Miconazole, Trirnethoprim, Methotrexate, Metronidazole, Sulfametoxazole.

The term "*Sulfolobus* promoter" relates to the promoters of the *Sulfolobus* host cell wherein the expression vector is suppose to be used in. Preferable the promoters include the promoters of the following ORFs: tf55alpha, tf55beta, tf55gamma, lacS, $T_{ind}$, SSV1-integrase, pyrEF, 16S ribosomal gene, UV-/heat-shock-/or otherwise inducible promoters of known, unknown or hypothetical proteins. In addition, the nucleotide sequences of the promoter may contain 2, 3, 4, 5, 6, 7, 8, 9, 10, 11, 12, 13, 14 or up to 15 mutations as long as these mutations do not abrogate the nucleotide sequence's function as an inducible promoter. The term "restriction enzyme recognition site" refers to a motif on the DNA recognized by a restriction enzyme. Preferable the restriction enzyme and its recognition site are selected from the group consisting of AatII, AccI, Acc65I, AciI, AclI, AfeI, AflIII, AflIIII, AgeI, AhdI, AluI, AlwI, AlwNI, ApaI, ApaLI, ApoI, AscI, AseI, AsiSI, AvaI, AvaII, AvrII, BaeI, BamHI, BanI, BanII, BbsI, BbvI, BbvCI BceAI, BcgI, BciVI, BclI, BfaI, BfrBI, BfuAI, BglI, BglII, BlpI, Bme1580I, BmgBI, BmrI, BpmI, BsaI, BsaAI, BsaBI, BsaHI, BsaJI, BsaWI, BsaXI, BseRI, BsgI, BsiEI, BsiHKAI, BsiWI, BslI, BsmI, BsmAI, BsmBI, BsmFI, BsoBI, Bsp1286I, BspCNI, BspDI, BspEI, BspHI, BspMI, BsrI, BsrBI, BsrDI, BsrFI, BsrGI, BssHII, BssKI, BssSI, BstAPI, BstBI, BstEII, BstF5I, BstNI, BstUI, BstXI, BstYI, BstZ17I, Bsu36I, BtgI, BtrI, BtsI, Cac8I, ClaI, DdeI, DpnI, DpnII, DraI, DraIII, DrdI, EaeI, EagI, EarI, EciI, EcoNI, EcoO109I, EcoRI, EcoRV, FauI, Fnu4HI, FokI, FseI, FspI, HaeII, HaeIII, HgaI, HhaI, HinP1I, HincII, HindIII, HinfI, HpaI, HpaII, HphI, Hpy99I, Hpy188I, Hpy188III, HpyCH4III, HpyCH4IV, HpyCH4V, KasI, KpnI, MboI, MboII, MfeI, MluI, MlyI, MnlI, MscI, MseI, MsII, MspI, MspA1I, MwoI, NaeI, NarI, NciI, NcoI, NdeI, NgoMIV, NheI, NlaIII, NlaIV, NotI, NruI, NsiI, NspI, PacI, PaeR7I, PciI, PflFI, PflMI, PleI, PmeI, PmlI, PpuMI, PshAI, PsiI, PspGI, PspOMI, PstI, PvuI, PvuII, RsaI, RsrII, SacI, SacII, SalI, SapI, Sau96I, Sau3AI, SbfI, ScaI, ScrFI, SexAI, SfaNI, SfcI, SfiI, SfoI, SgrAI, SmaI, SmlI, SnaBI, SpeI, SphI, SspI, StuI, StyI, SwaI, TaqI, TfiI, TliI, TseI, Tsp45I, Tsp509I, TspRI, Tth111I, XbaI, XcmI, XhoI, XmaI and XmnI. The term "multiple cloning site" refers to an array of two and more of the above-listed restriction enzyme recognition sites and also includes other recognition sites known to the person skilled in the art which are not listed here.

The vector of the present invention allows to successfully and with high efficiency transform *Sulfolobus* cells, which are a model organism for hyperthermophilic Crenarchaeota. The combination with viral components and a virus-based mode of DNA transfer permits to reach cells, after the initial transformation event, by a process of infection, thereby resulting in a dramatically increased efficiency of transformation. This is achieved by expressing virus structural proteins that are capable of interacting with the packaging signal of the virus and, hence, of specifically packaging DNA attached to the packaging signal. The released viral particles contain a more of less "normal" viral coat, filled with the DNA of the expression vector. The released particles can subsequently enter new cells by infection which is generally much more efficient than the process of transformation. The presence of two origins of replications allows to propagate the vector both in *E. coli* and in *Sulfolobus*. The marker genes, permit selection of successfully transformed cells, stably harbouring the DNA of the expression vector. Since the expression vector of the present invention also provides a reported gene, successful transformation can conveniently be monitored by determining the expression from said reporter gene. As the reporter function is available shortly after transformation, time consuming DNA-preparation and Southern Blot analyses are not required. In addition, the presence of a selection marker and of the reporter function. permit a straightforward approach to the identification and selection of interesting clones.

In a preferred embodiment of the invention, the expression vector contains a *Sulfolobus* origin of replication which is selected from the group consisting of SSV1, SSV2, pSSVx and pRN plasmids (Palm et al., 1991; Schleper et al., 1992; Keeling et al., 1996; Zillig et al., 1994; Arnold et al., 1999).

The plasmids pRN1 and pRN2 amongst others belong to one family of plasmids (Keeling et al., 1996; Zillig et al., 1994; Arnold et al., 1999). The name pRN refers to the natural host, *Sulfolobus* islandicus RN1H1.

The plasmid pSSVx is defined as a hybrid between a plasmid and a fusellovirus. This plasmid, in the presence of a helper (SSV1 or SSV2) is able to spread as a virus satellite via virus-like particles. Like pRN1 and pRN2, pSSVx belongs to the pRN family of Sulfolobus plasmids, as judged by its genome organization, by the high sequence similarity of a cluster of ORFs and two putative replication origins that comprise 50%-70% of their genomes. However, a tandem array of two ORFs in a non-conserved region in pSSVx is clearly homologous to a similar tandem of ORFs of as yet unknown function in SSV2 and SSV1, suggesting a viral origin for these plasmid ORFs. The plasmids pRN1 and pRN2, which lack these ORFs, do not spread with the help of SSV1 or SSV2, indicating that a sequence element in this cluster is essential for the packaging and spreading of pSSVx.

The vector of the present invention contains a sulfolobus promoter followed 3' by a restriction enzyme recognition site or a multiple cloning site for insertion of a gene of interest and optionally a 3' regulatory element. Preferentially, the vector contains an attachment site for insertion of a gene of interest. In that case, the gene of interest is preferentially inserted by homologous recombination. The term "attachment site" refers to a sequence either important for recombination of the virus, or its derivatives, into the host chromosome. In particular, the term "attachment site" also refers to artificially added DNA stretches which may flank both 5' and 3' ends of a gene of interest, promoter, selectable marker, termination sequences or sequence tags, amongst others, within the vector of the present invention which are used for targeted exchange by in vitro recombination with another sequence of interest flanked by homologous attachment sequences.

In another preferred embodiment of the invention, the expression vector contains the complete genome of SSV1 or SSV2 or chimeras thereof, thereby providing the *Sulfolobus* origin of replication, the packaging signal and the genes encoding the structural proteins VP1 and VP3 and the integrase of SSV1 or SSV2. In another preferred embodiment of the invention, the expression vector contains the genome of SSV1 or SSV2, wherein the genome contains deletions, substitutions or mutations. Preferable, the depleted viral genome contains in addition to the structural proteins and the integrase gene at least one open reading frame selected from the group consisting of a100, a132, c80, a79, a45, c102b, b129, a291, c124, c792, b78, c166, b115, a82, a84, a92, b277, a153, b251, d335, d244, e178, f93, d63, b49 and e51 (Stedman et al., 2003). All other ORFs occur in both genomes of SSV1 and SSV2.

In yet another preferred embodiment of the invention, the selectable marker gene of the expression vector encodes an essential protein of *Sulfolobus*. In a more preferred embodiment of the present invention, the essential gene is a gene of the de novo nucleotide anabolism, a gene of the aminoacid biosynthesis or a gene conferring antibiotic resistance. In another more preferred embodiment, the vector contains orotidine-5'-monophosphatase pyrophosphorlyase and orotidine-5'-monophosphatase decarboxylase (pyrEF) as selectable marker genes (Martusewitsch et al. 2000).

In a preferred embodiment of the invention, the expression vector contains 3' to the translation initiation site of the promoter for the expression of the gene of interest additional nucleic acid sequences so that the expressed protein has an N-terminal extension. In a more preferred embodiment, the N-terminal extension is (a) a signal sequence directing the secretion of the expressed protein; or (b) a tag for purification; or (c) a tag for specific detection. The sequence encoding the polypeptide may be fused to a marker sequence, such as a sequence encoding a peptide which facilitates purification of the fused polypeptide or which provides a signal for intracellular transport of the protein. Accordingly, the polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al, *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al, *Cell* 37: 767 (1984).

In another preferred embodiment, the promoter for the expression of the gene of interest is a constitutive promoter selected from the group consisting of genes involved in central metabolisms and information processing such as the promoters of the ribosomal subunits 16S, 23S rRNA or the promoters of polymerases, transcription, replication or translation factors.

In a further preferred embodiment of the invention, the promoter for the expression of the gene of interest is an inducible promoter and may be selected from the group consisting of (a) heat inducible promoters Tf55alpha, TF55beta, TF55gamma, hsp20, htrA, (b) cold inducible promoters TF55gamma and (c) promoters inducible by a carbon source such as arabinase, trehalose, maltose, galactose, sucrose.

In yet a further preferred embodiment of the invention the vector contains an additional expression cassette for a reporter protein, selected from the group consisting of β-galactosidase, luciferase, green fluorescent protein and variants thereof.

The present invention also relates to a shuttle vector comprising the sequences of the expression vector of the invention and additional sequences for propagation and selection in *E. coli*, wherein the additional sequences comprise (a) an *E. coli* ori of replication; and (b) a marker for selection in *E. coli*. In a preferred embodiment of the invention, the marker of selection is a protein that confers resistance to selected from the group consisting of ampicillin, kanamycin, chloramphenicol, tetracyclin, hygromycin, neomycin or methotrexate.

The present invention also relates to a host cell transformed with the expression vector of the invention, wherein the host cell is *E. coli* or sulfolobus. In a preferred embodiment of the invention, *Sulfolobus* comprises the species *Sulfolobus acidocaldarius*, *Sulfolobus brierleyi*, *Sulfolobus hakonensis*, *Sulfolobus metallicus*, *Sulfolobus shibatae*, *Sulfolobus solfataricus*. Preferred *E. coli* strains are BL21, BL21(DE3) or BL21(DE3)pLysS and BL21 derivatives, HB101, JM109 and derivatives, XL-1blue and derivatives, DH10B, DH12S, DH5alpha and derivatives, DB3.1, Stb14, TOP10 and derivatives.

In a preferred embodiment of the invention the transformed expression vector provides a gene encoding an essential protein. In a more preferred embodiment the essential gene is a gene of the de novo nucleotide anabolism, a gene of the aminoacid biosynthesis or a gene conferring antibiotic resistance. In another more preferred embodiment, the essential genes are orotidine-5'-monophosphatase pyrophosphorlyase and/or orotidine-5'-monophosphatase decarboxylase. In another preferred embodiment of the invention, the host is deficient in expressing a fully functional version of said essential gene provided by the expression vector. As a consequence, the host cell can only survive if the essential protein is provided by expression from the expression vector.

The present invention also relates to a method of producing a polypeptide, comprising culturing the host cell of the present invention under suitable conditions and isolating said polypeptide from the cells or the cell culture supernatant.

The present invention also relates to a method of generating infection recombinant subviral particles composed of SSVx or derivatives thereof, wherein SSVx is propagated with the help of a complete virus SSV1 or SSV2. In a preferred embodiment, the methods of the present invention comprises generating infectious recombinant subviral particles composed of the structural proteins of SSV1 and/or SSV2, having packaged the DNA of the expression vector of the present invention, wherein the method has the steps of (a) introducing the DNA of the expression vector and the DNA of SSV1 or SSV2 into a host cells; (b) incubating the cells for time and under conditions sufficient to allow replication of SSV1 or SSV2 and spreading in the cell culture; (c) harvesting the cell culture supernatant or the host cells.

The present invention also relates to the use of the vector of the present invention for expression of RNAi or antisense RNA, wherein Sulfolobus promoters of the vector are used for transcription of a gene or parts of a gene either in antisense or sense orientation or in both orientations. In a preferred embodiment of the present invention's use, the expression vector is used in gene silencing, comprising gene. silencing by antisense RNA-or gene silencing by double stranded RNA ($RNA_i$).

Finally, the present invention relates to a kit comprising (a) the vector of the present invention, (b) the host cell of the present invention, and/or (c) a host cell deficient in the expression of the essential protein, in one or more containers.

The figures show:

FIG. 1: The figure shows a map of pMJ02a (A) and of pMJ03bx (B), highlighting some recognition sites for restriction enzyme and the relative positions of the pUC18 region, of the reported gene lacS and of the selection marker pyrEF.

FIG. 2: Detection of successful transformation with the expression vector by using an X-Gal assay. Cells in solution (A) or cells grown on gelrite plates (B) are shown.

Figure 3:
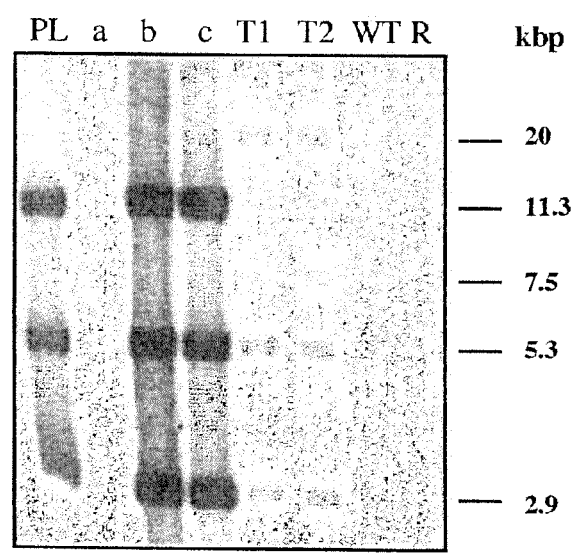

FIG. 3: Schematic representation by Southern analysis of the extent of transformation of the primary transformation mixture with a recombinant plasmid and of the integration of the recombinant vector into the chromosome of Sulfolobus solfataricus.

Figure 4:
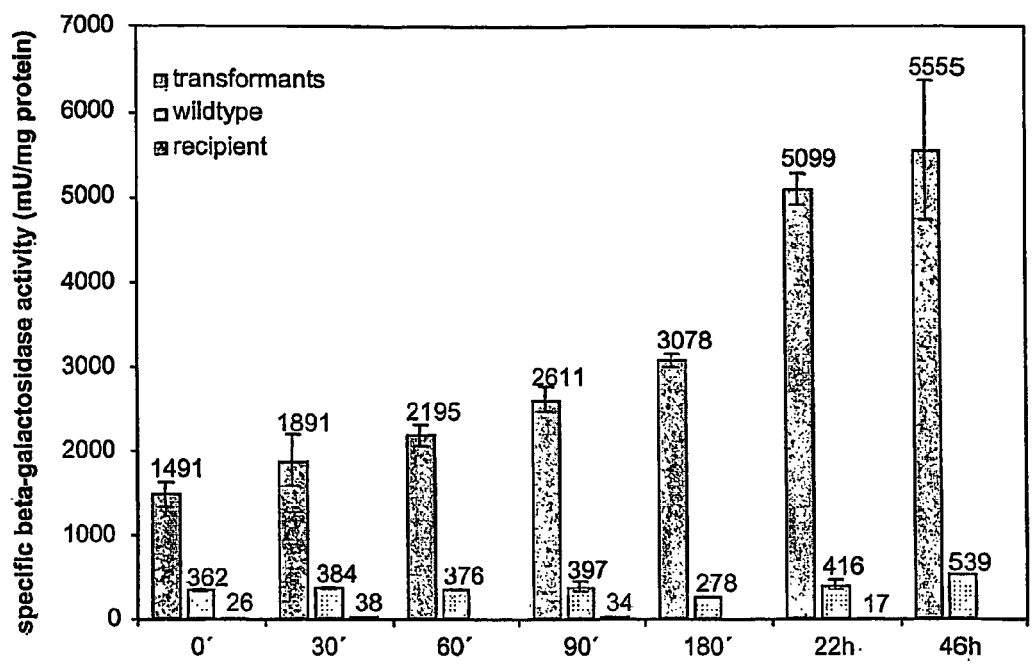

FIG. 4: Specific beta-galactosidase activities in transformants and wild-type cells of Sulfolobus solfataricus after heat shock at 88° C.

Figure 5:
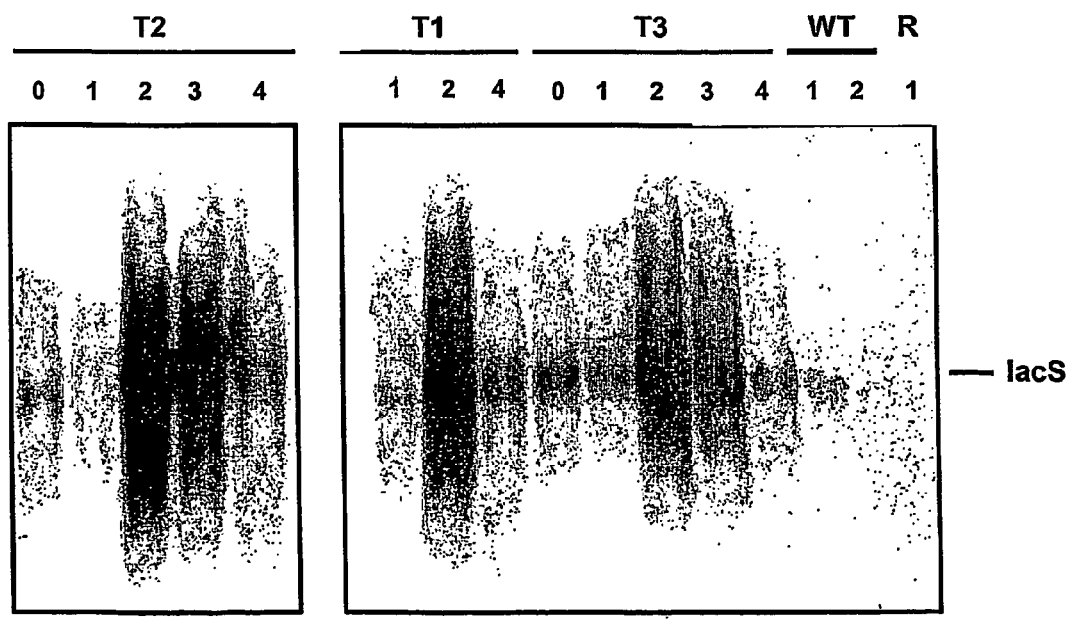

FIG. 5: Representative Northern analysis for the detection of the lacS transcript after 0 min (0), 30 min (1), 90 min (2) and 22 h (3) of heat shock and 17 h after UV induction (4). Equal amounts (5 μg) of total RNA from transformants T1, T2, T3, from the wild type (WT) and from the recipient (R) were separated on a 1.2% agarose gel and hybridized with a specific lacS probe. The detected fragment size is 1.6 kb.

Figure 6:
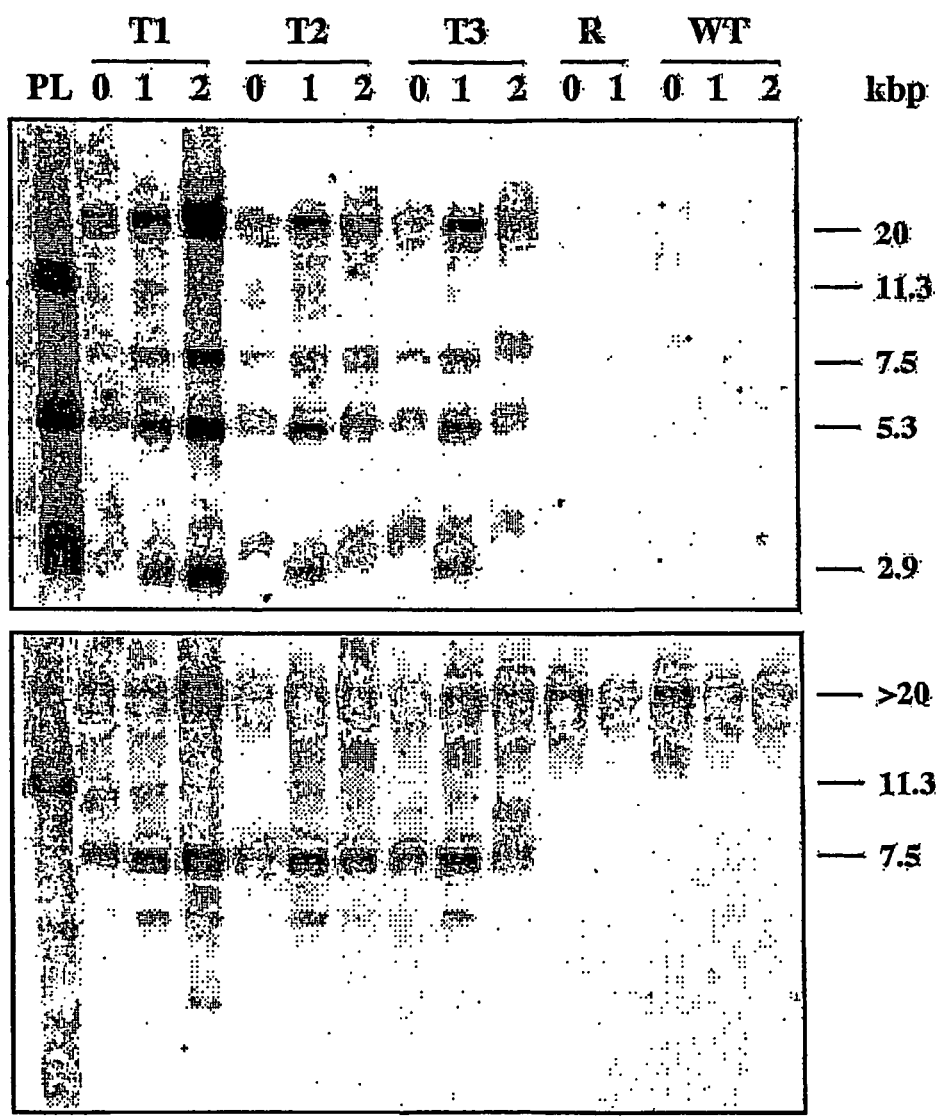

FIG. 6: Isolation of total DNA from h eat-induced and not heat-induced cultures. Hybridization with SSV1- and/or lacS-specific probes (FIG. 6A, B). Correlation of detected amounts of DNA with results of activity assays or Northern analyses, respectively, for the exclusion of a gene dosage effect.

Figure 7A:
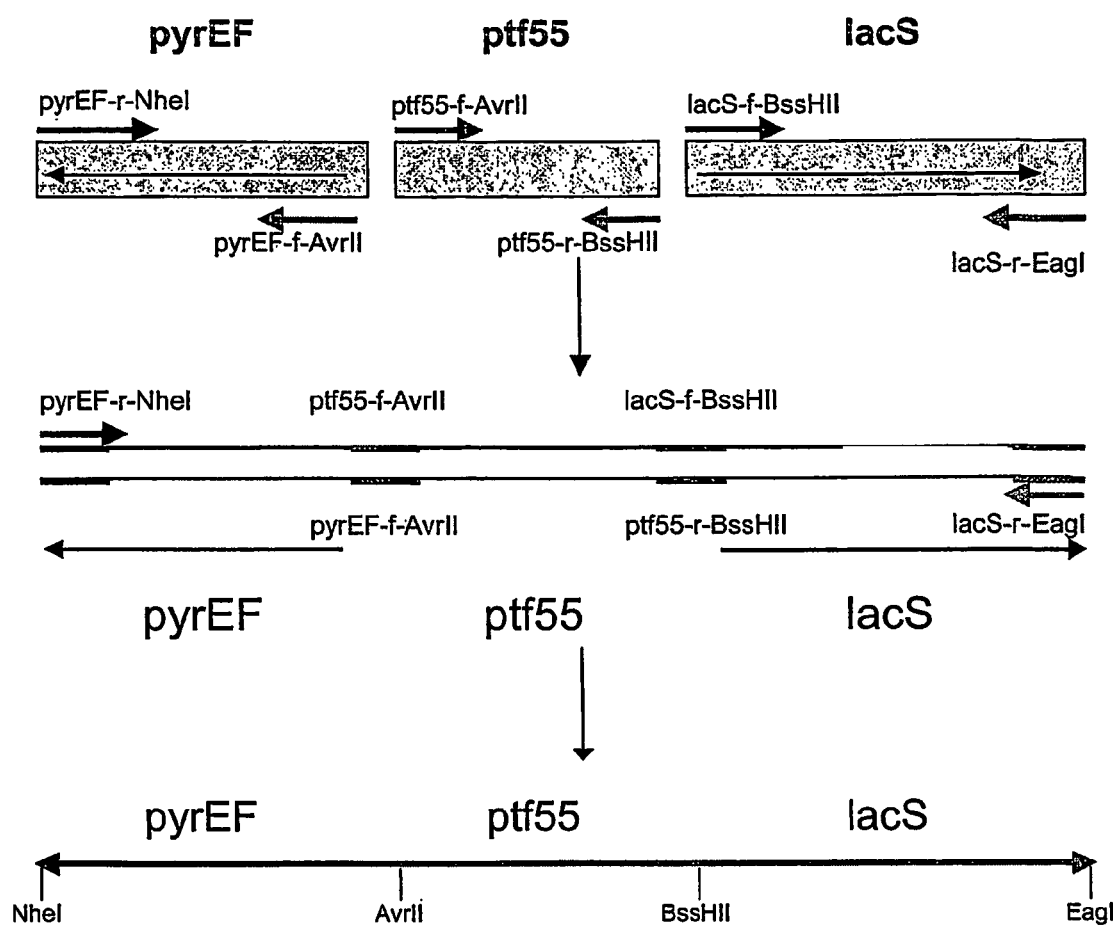

FIG. 7:

FIG. 7a: Fusion of the selection marker pyrEF, the promoter of the alpha subunit of the thermosome (ptf55) and the reportergene, lacS of Sulfolobus within two PCR reactions.

First the single genes of pyrEF and lacS as well as the promoter region, pff55 were amplified using pMJ03bX as DNA template. The primers pyrEF-f-AvrII and pff55-f-AvrII were completely complementary as well as the primers ptf55-r-BssHII and lacS-f-BssHII. Because of these complementary overhangs it was possible to fuse the single products and to amplify the fusion within a second PCR using only the flanking primers pyrEF-r-NheI and lacS-r-EagI. The resulting PCR product is composed of pyrEF, pff55 and lacS flanked by recognition sites for NheI and EagI. The single components of the cassette are separated from each other by recognition sites for AvrII and BssHII.

The orientation of the genes in the cassette is indicated by arrows. Complementary primers are shown in same colour.

Figure 7B:
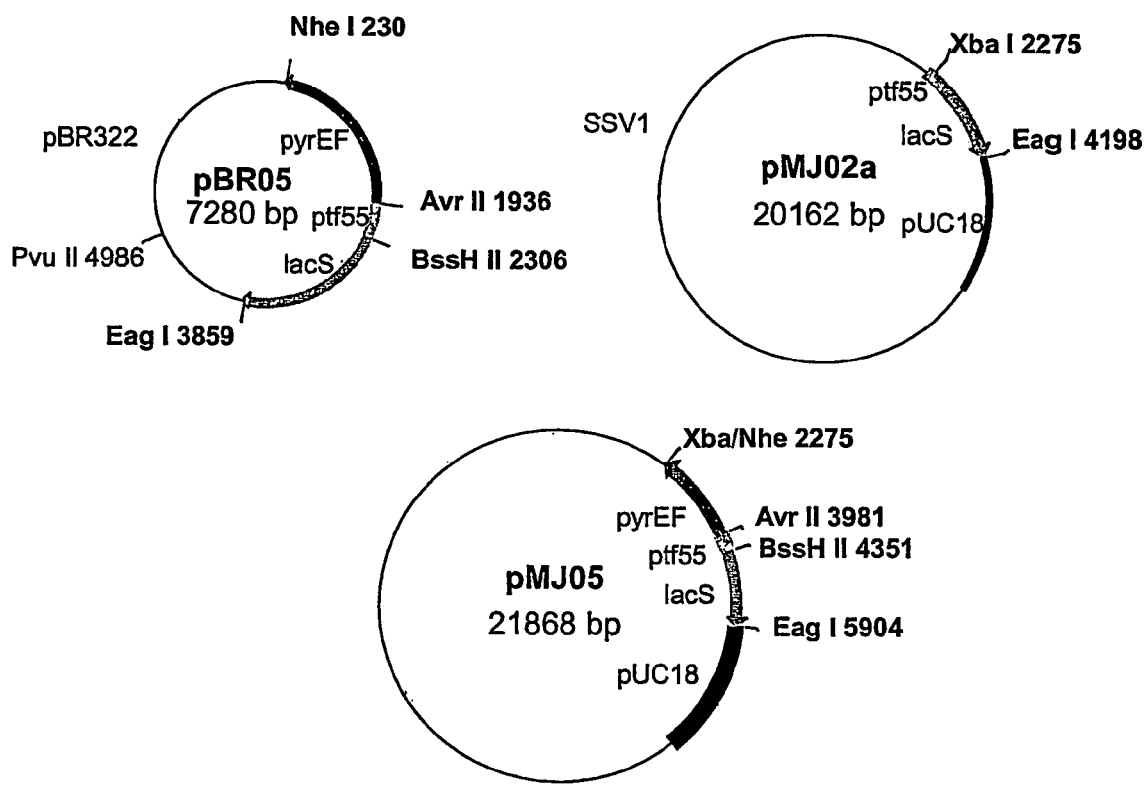

FIG. 7b pBR05 is a E. coli vector containing a cassette composed of the selection marker pyrEF, the promoter pff55 and the reporter gene lacS of Sulfolobus solfataricus. The cassette is flanked by recognition sites for NheI and EagI. In addition the selection marker is seperated from the promoter by AvrII as well as the promoter is seperated from the reporter-gene by BssHII.

pMJ02a is a E. coli/Sulfolobus shuttle vector, containing replication origins for both organisms. This vector consists of pUC18, a fusion of pff55 and lacS flanked by recognition sites for XbaI and EagI, which can be used to introduce the pyrEF-pff55-lacS cassette of pBR05.

pMJ05 is a E. coli/Sulfolobus shuttle vector, containing replication origins for both organisms. In contrast to pMJ02a this vector contains recognition sites for Avril which separates the pyrEF genes from pff55 and BssHII which seperates ptf55 from lacS

Figure 8A:

FIG. 8:

FIG. 8a: E. coli/Sulfolobus shuttle vector pMJ05-sor, containing the selection marker pyrEF, the promoter, ptf55, of Sufolobuus and the gene of the sulfur oxygenase reductase (sor) of Acidianus ambivalens. The promoter gene cassette is shown separately. Recogintion sites for AvrII, BssHII and EagI are indicated as well as the strep-tag at the C-terminus of the sor.

FIG. 8b: A) SDS-PAGE of crude extracts of pMJ05-sor transformants, eluent of strep-tactin column and wt-SOR (control). Marker bands are indicated by size.

B) SOR-activity plot from strep-tactin eluent of pMJ05-sor transformants showing the time dependent increase of the products thiosulfate and hydrogen sulfide formed by the oxygenase and reductase activity of the SOR FIG. 9: E. coli/Sulfolobus shuttle vector pSVA6 containing the gene sso2316 of Sulfolobus solfataricus encoding a secretion ATPase fused to a his-tag located at the N-terminus of the gene. The cassette containing the promoter, ptf55, fused to the flaI gene is shown in more detail. Recognition sites for AvrII, BssHII, ApaI and EagI are indicated as well as the position of the his-tag. To ensure transcription termination of the flaI gene an ApaI site was introduced which is followed by the putative transcription termination sequence of the lacS-gene which was replaced.

FIG. 10: Membrane fractions of Sulfolobus solfataricus recipitent (M16) and pSVA6 transformants before (0) and after heat shock for 2, 6 hours (a,b) and 1 and 2 days (c) separated on SDS-PAGE. Coomassie stained (a) and western-blot analyses with anti-his tag (b) and anti-FlaI antibodies (c) used for detection. The size of flaI is indicated by arrows. Positive control: His tagged protein (+).

FIG. 11: E. coli/Sulfolobus shuttle vector pSVA9. The cassette containing the promoter Para and lacS reporter gene is shown in more detail. As shown in more detail a NcoI recognition site was introduced directly on the ATG-start of lacS. Recognition sites for AvrII, NcoI, ApaI and EagI are indicated.

FIG. 12: Specific beta-galactosidase activity of two single pSVA9 transformants (T1, T2). Liquid cultures were grown in glucose minimal medium (control) and in. parallel with 0.4% D-arabinose (induced). The optical density (blue lines) as well as the specific β-galactosodase activity (red panels) was determined for 0, 6, 12, 24, 35, 54 and 74 hours.

FIG. 13: in vitro recombination of expression vector pSF02.

FIG. 14: Construction of a destinationvector pSF01.

FIG. 15: a) Expression-shuttle vector pSF02;
b) detailed drawing of the expression cassette.

FIG. 16: Growth curve of Sulfolobus solfataricus pSF02 in selection medium (−Uracil).

FIG. 17: Southern-Blot-analysis of Sulfolobus solfataricus pSF02
A) pSF02 control DNA;
B) *Sulfolobus* solfataricus pSF02 clone 1 (total DNA)
C) *Sulfolobus* solfataricus pSF02 clone 1 (total DNA)
The examples illustrate the invention:

EXAMPLE 1

Construction of the Shuftle-Vectors pMJ02a and pMJ03bX

For the construction of pMJ02a. (FIG. 1A), the. 1.5 kbp lacS ORF was PCR amplified from chromosomal DNA of *S. solfataricus* P1, using the primer lacS2.F (SEQ ID NO: 1. (GCTCCAGTCATGTACTCATTTCCAAATAGC) and LacS-Eag (SEQ ID NO: 2. (GAAACGGCCGGCMTCT-MTG). The promotor region, including the first 5 codons of the open reading frame of tf55α were also PCR amplified from chromosomal DNA of *S. solfataricus* P1, using the primers TF55prom.F-Eag (SEQ ID NO: 3. (ATTAAGTCG-GCCGTCMGAAA) and TF55prom2.R (SEQ ID NO: 4. (TGAGTACATGACTGGAGCTGCCATACC). Both PCR products obtained were used in a second PCR-reaction, using the primers TF55prom.F-Eag and LacS.R-Eag. By using overlapping complementary sequences of TF55prom2.R and LacS2.F in this second PCR reaction, the TF55α-Promotor was fused to the lacS-ORF and was subsequently amplified. The resulting 2055 bp PCR product was cleaved by EagI and cloned into pBluescriptSK+. After sequence analysis, the fragment was isolated from the vector as a PstI (dephosphorylated) and SacI fragment and ligated to pUC18 (PstI/SacI and dephosphorylated) and SSV1 (PstI) in a ligation of three fragments.

pMJ03bX (FIG. 1B) was obtained by PCR-amplifikation of the pyrEF Gene using chromosomal DNA of *S. solfataricus* P1 and the primers pyrEF.F-Nhe (SEQ ID NO: 5. (TCTCGCTAGCGMTMTGCTGCCC) and pyrEF.R-NheI (SEQ ID NO: 6. (TTACGCTAGCTTCCTCGTGTAGAT) and ligation, after NheI-cleavage, into pMJ02a (XbaI, dephosphorylated). After electroporation of *E. coli* DH10B positive clones were identified by colony hybridisation with a SSV1-specific probe and a lacS-specific probe. The plasmids isolated from *E. coli* were characterized by restriction analysis and the orientation of the insert was determined.

EXAMPLE 2

Transformation of *Sulfolobus*

Electroporation was performed under optimized conditions according to a previously established protocol for *Sulfolobus* (Schleper, 1992). Electroporation-competent cells are prepared from a 50 ml over night culture ($OD_{600nm}$=0.1 to 0.3). The cells are cooled on ice and centrifuged for 15 min at 4.000 rpm and 4° C. The cell pellet is subsequently washed with 50, 25 and 1 ml of pre-cooled 20 mM sucrose to remove salts from the cell culture medium. Using 20 mM sucrose, the cells are adjusted to a concentration of $10^{10}$ cells/ml. Prior to electroporation, the competent cells are kept on ice. 50 μl of cell suspension are carefully mixed with 0.25 to 1.5 μl of a dialyzed plasmid-DNA suspension (max. 300 ng DNA) and transferred to a pre-cooled electroporation cuvette (distance of electrode: 0.1 cm, BIO-RAD). Electroporation is performed by using a Gene Pulser (Bio-Rad), using the following settings:
Voltage 1.5 kV
Capacitiy 25 μF
Resistance 400 Ω

Immediately after electroporation the cells are transferred to 1 ml growth media, in 1,5 ml reaction tube, and shaked for 1 to 2 h on a heating plate at 75° C., with occasional aeration. Subsequently, the transformed cells are transferred to 50 ml of medium.

EXAMPLE 3

Detection of Transformants in the Primary Transformation Mixture and at the Level of Single Transformants After the transformation of *Sulfolobus* mutants, transformants could be detected qualitatively already in the transformation mixture approx. 3 days after electroporation. A blue stain obtained after incubation at 78° C. of a culture aliquot (approx. 800 μl) with 100 μl X-Gal (5 mg/ml) indicates successful transformation, the blue staining resulting from cleavage of X-Gal and release of the chromophor (FIG. 2A). Single transformants can reliably be identified and isolated by their blue stain after adding X-Gal to single colonies grown from primary transformation mixtures on Gelrite plates and, if necessary, incubating them at 78° C. (FIG. 2B).

The initial extent of transformation of the primary transformation mixture with the recombinant plasmid and the chromosomal integration in single transformants are detected by Southern analysis of total DNA isolated from the primary transformation mixture and of single transformants and by hybridization with a SSV1-specific probe (FIG. 3).

Schematic representation by Southern analysis of the extent of transformation of the primary transformation mixture with a recombinant plasmid and of the integration of the recombinant vector into the chromosome of *Sulfolobus solfataricus*.

For the purpose of hybridization with a SSV1-specific probe, total DNA isolated from a primary transformation mixture 3 days (a), 4 days (b) and 5 days (c) after electroporation as well as from single transformants (T1, T2), from the wild type *Sulfolobus solfataricus* P1 and from the recipient (R) was cleaved hydrolytically with PvuII. PL designates the recombinant vector isolated from *E. coli*.

At the beginning, the recombinant virus spreads rapidly in the primary transformation mixture and is therefore detectable only in its plasmid form (lane a, b, c) whereas in isolated single transformants, the virus is detectable only its form as integrated into the chromosome. The 20 kbp and the 7.5 kbp fragment represent the right and left element of the integrated vector, whereas the plasmid-specific 11.3 band is not any more detectable in single transformants (cf. also FIG. 6).

EXAMPLE 4

Regulation Studies

Using the newly developed vector, the regulation of gene expression in hyperthermophile Archaea was analyzed in vivo.

Analysis of the Regulation Mechanisms of the TF55α Promoter in Case of Heat Shock Induction Single transformants grown in liquid culture up to an OD 600 nm of 0.2-0.3 are incubated for different periods of time (30 min to 46 h) at 88° C. The induction of lacS expression caused by heat shock and performed by the inducible promoter is quantified by subsequent β-galactidose activity assays (FIG. 4). Raw cell extracts are obtained as follows:

Cell pellets obtained from 5-10 ml cell culture are re-suspended in approx. 100 µl 10 mM Tris/HCl buffer, pH 8 and lysis is performed by freezing at −80° C. for 10 min and thawing at 50° C. (5 min). This procedure is repeated four times and the obtained extract is centrifuged at approx. 10000 g for 30 min. The supernatant is either used immediately for an enzyme assay or stored at −80° C. The protein concentration of the raw extracts is measured in a Bradford assay.

The β-galactidose assay is performed according to Pisani et al. (1990). 10 µl extract are transferred into a pre-heated quartz cuvette (75° C.) with 990 µl test buffer (2.8 mM 0-nitrophenyl β-D-galactopyranosid in 50 mM sodium phosphate buffer, pH 6.5). Hydrolysis of ONPG is monitored photometrically by the increase of absorption at 405 nm. One Unit is defined as the amount of enzyme, which catalyses the hydrolysis of 1 µmol ONPG/min at 75° C. The molar absorption coefficient of ONPG at these conditions is 3100 $M^{-1} \times cm^{-1}$.

Northern Analyses: Detection of Induced lacS-mRNA with a lacS.Specific Probe in Heat-Induced Cultures Compared to Non-Induced Cultures.

Total RNA is isolated using the Rneasy kit (Qiagen) and treated subsequently with DNase I. For the purpose of transcript analysis, 5 µg RNA are separated on a denaturing agarose containing 1.2% (w/v) formaldehyde and subsequently transferred to a nylon membrane. A lacS-specific probe is prepared with the T3/T7 system. pBluescript with inserted tf55-lacS fusion, hydrolytically cleaved with Pag I, is used as a template. The probe is labeled with digoxigenin (DIG RNA labeling kit, Roche).

Representative Northern analysis for the detection of the lacS transcript after 0 min (0), 30 min (1), 90 min (2) and 22 h (3) of heat shock and 17 h after UV induction (4). Equal amounts (5 µg) of total RNA from transformants T1, T2, T3, from the wild type (WT) and from the recipient (R) were separated on a 1.2% agarose gel and hybridized with a specific lacS probe. The detected fragment size is 1.6 kb.

The comparison of transcript amounts in transformants and the wild type shows that the tf55 promoter, which regulates the recombinant lacS, causes an increased transcription of lacS, which furthermore is inducible by heat. After a 90 min heat shock a strong increase of lacS transcript is observed, which is detectable also after a 22 h heat shock.

Control Experiment for the Exclusion of Increased Activities or Transcript Amounts, Respectively, Caused by a Gene Dosage Effect, Using DNA Analysis (Southern analysis). Isolation of Total DNA from Heat-Induced Cultures and from not Heat-Induced Cultures.

Isolation of Total DNA from *Sulfolobus*:

3 ml or 50 ml, respectively, of a culture in the exponential growth phase were pre-cooled on ice for a few minutes and 15 minutes centrifuged at 4000 rpm. The cells are re-suspended in 500 µl or 5 ml, respectively, TE buffer and incubated at room temperature for 30 min after adding N-laurylsarcosin (final concentration 0.8%) and Triton X-100 (final concentration 0.06%).

After lysis of the cells, the proteins are extracted three times with a phenol/chloroform/isoamyl alcohol mixture (25: 24:1). The DNA is precipitated during 20 min at −20° C. after adding 3M sodium acetate solution (¹/₁₀ of the volume) and ice cold 100% ethanol (2 to 2.5 volumes). Subsequently, the DNA is centrifuged at 15000 rpm and 4° C. for 30 min, washed once with 70% ethanol, air dried and taken up in a suitable volume TE buffer with 10 µg/ml RNase A Isolation of Total from Heat-Induced and not Heat-Induced Cultures. Hybridization with SSV1- and/or lacS-Specific Probes (FIG. 6A, B). Correlation of Detected Amounts of DNA with Results of Activity Assays or Northern Analyses, Respectively, for the Exclusion of a Gene Dosage Effect.

Southern analysis of the transformants (T1, T2, T3), of the recipient (R) and of the wild type (WT) after 0 min (0), 30 min (1) and 90 min (2) heat shock. Total DNA was cleaved hydrolytically with Pvull and hybridized with a SSV1-specific probe (A) and a lacS-specific probe. PL denotes plasmid DNA of the recombinant vector isolated from *E. coli*, hydrolytically cleaved with Pvull. It is demonstrated that the heat shock does not lead to an increase of recombinant vector and an increase in activity is not due to a gene dosage effect.

EXAMPLE 5

Construction of the Shuttle-Vector pMJ05

For the construction of pMJ05, the *Sulfolobus* selection marker pyrEF, the promoter of the alpha subunit of the thermosome, TF55 (pff55) and the reporter-gene (beta-galactosidase, lacS of *Sulfolobus*) was amplified in a first PCR using pMJ03bX as template DNA. The PCR products obtained (pyrEF, pff55 and lacS) were used as templates in a second PCR. Thereby the single PCR products pyrEF and pff55 as well as ptf55 and lacS were fused to each other because of the complementary overhangs introduced by the primers used in the first PCR. During the second PCR reaction the fusion pyrEF-pff55-lacS was amplified by using the flanking primers pyrEF-r-NheI and lacS-r-EagI (see scheme in FIG. 7*a*).

The obtained PCR products were cleaved by using NheI and EagI and ligated into pBR322 plasmid which also had been cleaved using NheI and EagI. The obtained construct pBR05 was again cleaved by using NheI and EagI in order to unhinge the cassette out of the vector and subsequently digested using Pvull. By using Pvull the desired pyrEF, pff55, lacS cassette was easy to distinguish in size from the pBR322 fragment. After isolation of the cassette it was ligated into pMJ02a cleaved by XbaI and EagI and dephosphorylated before resulting in the *E. coli/Sulfolobus* shuttle vector pMJ05; see FIG. 7*b*.

EXAMPLE 6

Uses of the Vector-Systems of the Invention

Expression of the Sulfur Oxygenase-Reductase Derived from Acidianus Ambivalens:

The gene of the sulfur oxygenase-reductase, which has an approximate size of 1 kb, was amplified by PCR. The primers used therefore introduced a BssHII recognition site at the N-terminus and an EagI recognition site at the C-terminus of the gene. As template DNA a vector was used which carries the sor-gene fused to a strep-tag at the C-terminus. The tag was part of the amplified product in order to enable an isolation of the gene product using strep-tactin affinity chromatography. The PCR product was cleaved using BssHII and EagI and ligated into the vector pBR05. The expression cassette (consisting of pyrEF, ptf55 and sor; see schema in FIG. 8*a*) was subsequently excised out of the pBR05-sor construct using NheI and EagI. The fragment was ligated into the XbaI, EagI restricted and dephosphorylated pMJ02a, resulting in pMJ05-sor. A *Sulfolobus solfataricus* pyrEF/lacS double-mutant was transformed with the obtained construct. The heterologous expression was analyzed by SDS-PAGE as well as in an assay detecting the activity of the recombinant gene product (Kletzin 1989); see FIG. 8b.

Expression of the Membrane Associated FlaI Protein (Components of the Secretion ATPase) Derived from *Sulfolobus sofataricus*:

In analogy to the sor-cloning, described herein above, the flaI-gene (sso2316), which encodes one of five secretion ATPases of *Sulfolobus*, was cloned into a pre-vector and subsequently into the shuttle vector pMJ02a. The obtained expression cassette in which the flaI-gene further comprises at the N-terminus a his-tag is shown in FIG. 9. After transformation of the *Sulfolobus sofataricus* mutant M16 the heterologous expression of flaI was analyzed by SDS-PAGE and Western-analysis using his and fiaI specific antibodies; see FIG. 10.

Introduction of an Ara-Promoter:

The ara-promoter is an arabinose inducible promoter which enables high expression levels without stressing the transformed organism.

In a pBR05 derivate the promoter region of tf55 including the peptide leader was replaced by the promoter of the arabinose binding proten AraS. A NcoI recognition site was introduced directly on the ATG-start of lacS; see FIG. 11.

After cloning of the pyrEF-paraS-lacS cassette into pMJ02a the *Sulfolobus sofataricus* double-mutant M16 was transformed with the obtained construct pSVA9 and single colonies were isolated. The isolated clones were used for analyses of the strength of the ara-promoter under different growth conditions. These tests comprised the incubation of two single clones in liquid glucose minimal media. The cultures were then splitted in two parts and the separate cultures were subsequently incubated in the same minimal medium as before and in parallel induced with arabinose in a final concentration of 0.4%. The optical density of the cultures and the specific beta-galactosidase activity was analyzed at different time points. Thereby the induction of gene expression subsequent to the arabinose addition was demonstrated. As shown in FIG. 12, the expression level of beta-galactosidase is enhanced (8 times) by the addition of arabinose.

EXAMPLE 7

The construction of a modular expression shuttle vector with optional cassettes containing different promoters, genes of interest and tag-sequences is based on the site specific recombination of bacteriophage lambda (Landy 1989; Ptashne 1992). In this example, a modular DNA Fragment, consisting of the heat-inducible promoter TF55α and the reporter gene lacS with an N-terminal Myc-tag, was assembled by in vitro recombination. In a first step the three elements (promoter, Myc-tag and lacS) were amplified separately by PCR. Hereby, specific attachment sites (attB1 to attB4) were fused to the 5'- and 3'-ends of each PCR-product. In the following these PCR fragments were recombined in vitro with a donor vector using BP Clonase Enzyme mix forming entry vectors a, b and c. During these BP-specific recombinations specific attachment sites were formed (attL1 to attL4, FIG. 13A), that allowed a unidirectional fusion of all tree elememts with a destination vector (FIG. 13B) in the next step.

For the introduction of the thee elements of this expression cassette into the *Sulfolobus* shuttle vector system, the expression vector had first to be modified into a destination vector. For this purpose the pUC18/SSV1-hybridvector pMJ01 was ligated with the selection marker pyrEF and a recombination cassette containing the $Cm^R$-gene and the ccdB-gene. ccdB codes for an *E. coli* gyrase inhibitor, which is lethal for *E. coli* strains without resistance against ccdB and therefor allows negative selection. Furthermore the $Cm^R$/ccdB-cassette is flanked by attR3- and attR4-sites. For construction of this destination vector (pSF01) see FIG. 14.

In a final step the three entry vectors were recombined with the destination vector, where site specific recombination occurred between attR1 and attL1, attR2 and attL2, attR3 and attL3, and at least attR4 and attL4, using LR Clonase Enzyme Mix, leading to the expression vector pSF02 (FIG. 13C, FIG. 15a/b). All recombinational procedures were performed as described in the "Gateway instruction manual" (Invitrogen).

After transformation in *E. coli* and isolation of the DNA, pSF02 was transformed in the pyrEF/lacS-deficient *Sulfolobus solfataricus* PH1/M16 by electroporation. Transformants were screened for β-galactosidase activity as described in example 3. A blue color was detected after two days in culture medium at 78° C. *Sulfolobus solfataricus* lacS/pyrEF double mutant PH1/M16 was used as negative control. After transfering the cultures into selection medium (Brock's medium, Grogan, 1989, with 0.1% trypton and 0.2% arabinose as carbon source without uracil, pH 3) the (+)controll- and the (−)controll culture (*Sulfolobus solfataricus* PH1/M16 +/−uracil) showed the expected results. The culture of the transformed strain was able to grow without uracil, indicating a complementation of the uracil-auxotrophic mutant with pyrEF by pSF02 (FIG. 16).

To obtain single transformants the primary transformation mixture was incubated on gelrite plates with selection medium at 78° C. for 6 days. After exposure to X-Gal, pSF02 containing transformants showed a blue color due to beta-galactosidase activity of the reporter lacS. For identification of a recombination event between the *S. solfataricus* PH1/M16 chromosomal DNA and pSF02 two of these blue colonies were grown in selection medium for 6 days and total DNA was prepared from *S. solfataricus* using standard procedures (Stedman et al. 1999), restricted with Pvull and separated on a 1% agarose gel. Southern blot analysis of the DNA with a SSV1-specific probe showed a 20 kb and a 3.6 kb DNA fragment characteristic for integrated pSF02 into the chromosomal DNA of *S. solfataricus* besides the episomal vector fragments with 8.7, 7.4 and 2.9 kb in size (FIG. 17).

REFERENCES

Aagaard, C. et al. (1996) *FEMS Microbiol Rev* 18:93-104.
Aravalli, R. N. and Garrett, R. A. (1997) *Extremophiles* 1:183-191.
Arnold, H. P. et al. (1999) *Mol Microbiol* 34:217-226.
Bell, S. D. et al. (2001) *EMBO Rep* 2:133-138.
Bell, S. D., and Jackson, S. P. (2001) *Curr Opin Microbiol* 4:208-213.
Bouthier de la Tour, C. et al. (1990) *J Bacteriol* 172:6803-6308.
Cannio, R. et al. (1998) *J Bacteriol* 180:3237-3240.
Condo, I. et al. (1999) *Mol Microbiol* 34:377-384.
De Felice, M. et al. (1999) *J Mol Biol* 291:47-57.
Edgell, D. R. et al. (1997) *J Bacteriol* 179:2632-2640.
Elferink, M. G. et al. (2001) *Mol Microbiol* 39:1494-1503.
Elferink, M. et al. (1996) *FEMS Microb Letters* 137:31-35.
Gregor, D. and Pfeifer, F. (2001) *Microbiol* 147:1745-1754.
Grogan, D W. (1989) *J. Bacteriol.* 171, 6710-6719
Grogan, D. W. and Gunsalus, R. P. (1993) *J Bacteriol* 175: 1500-1507.
Hjort, K. and Bemander, R. (2001) *Mol Microbiol* 40:225-234.
Keeling, P. J. et al. (1996) *Plasmid.* 35:141-4.

Kletzin, A (1989) *J Bacteriol.* 171(3):1638-43.
Landy, A. (1989). *Annu. Rev. Biochem.* 58, 913-949.
Martusewitsch, E. et al. (2000) *J Bacteriol* 182:2574-2581.
Palm, P. et al. (1991) *Virology.* 185(1):242-50.
Patenge, N. et al. (2000) *Mol Microbiol* 36:105-113.
Pisani, F. M. et al. (1990). *Eur J Biochem* 187:321-328.
Ptashne, M. (1992). A Genetic Switch: Phage (Lambda) and Higher Organisms (Cambridge, Mass.: Cell Press).
Schafer, G. (1996) *Biochim Biophys Acta* 1277:163-200.
Schleper, C. et al. (1992) *Proc Natl Acad Sci USA* 89:7645-7649.
Schleper, C. et al. (1995) *J Bacteriol* 177:4417-4426.
She, Q. et al. (2001) *Proc Natl Acad Sci USA* 98:7835-7840.
Stedman K M. et al. (1999) *Genetics* 152, 1397-1405.
Stedman, K. M. Qunxin She, Hien Phan, Arnold, H. P., Holz, I., Garrett, R. A., Zillig, W. Relationships between fuselloviruses infecting the extremely thermophilic archaeon *Sulfolobus:* SSV1 and SSV2 Research in Microbiology, 2003, in press.
Vitagliano, L. et al. (2001) *EMBO J* 20:5305-5311.
Wadsworth, R. I. and White, M. F. (2001) *Nucleic Acids Res* 29:914-920.
Zillig, W. et al. (1994) *System Appl Micrbiol* 16: 609-628
Zillig, W. et al. (1998) *Extremophiles* 2:131-140.

The invention claimed is:

1. An isolated or a purified sulfolobus expression vector comprising:
   (a) a sulfolobus origin of replication;
   (b) coding sequences for structural proteins, a coding sequence for a site-specific integrase and a packaging signal wherein each of the structural protein coding sequences, the site-specific integrase coding sequence and the packaging signal are from one of SSV1, SSV2 or pSSVx and are operably linked to expression control sequences;
   (c) one or more selectable marker gene(s) encoding one or more essential proteins of sulfolobus, operatively linked to sulfolobus expression control sequences, wherein the essential proteins are orotidine-5'-monophosphates pyrophosphorlyase and orotidine-5'-monophosphatase decarboxylase; and
   (d) a sulfolobus promoter followed 3' by a restriction enzyme recognition site or a multiple cloning site within which, or adjacent to, is an inserted gene of interest, and the vector further comprises an optional 3' regulatory element.

2. The expression vector of claim 1, wherein the origin of replication is from one of SSV1, SSV2, pSSVx or pRN plasmids.

3. The expression vector of claim 1 or 2, wherein the vector contains the complete genome of SSV1, thereby providing said origin of replication, said packaging signal and the sequences encoding the structural proteins and the integrase of SSV1.

4. The expression vector of claim 1, wherein the vector contains a translation initiation site for the expression of the gene of interest.

5. The expression vector of claim 4, wherein the vector comprises additional nucleic acid sequences 3' of the translation initiation site so that the expressed protein has an N-terminal extension.

6. The expression vector of claim 5, wherein the N-terminal extension is
   (a) a signal sequence directing the secretion of the expressed protein;
   a tag for purification; or
   (b) a tag for specific detection.

7. The expression vector of claim 1, wherein the promoter for the expression of the gene of interest is a constitutive promoter, a promoter of a gene involved in central metabolism and information processing, a promoter of ribosomal subunit 16S, a promoter of ribosomal subunit 23S a polymerase promoter, a transcription factor promoter, a replication factor promoter or a translation factor promoter.

8. The expression vector of claim 1, wherein the promoter for the expression of the gene of interest is an inducible promoter.

9. The expression vector of claim 8, wherein the inducible promoter is selected from the group consisting of (a) a heat inducible promoters selected from the promoters of TF55alpha, TF55beta, TF55gamma, hsp20, or htrA, (b) a cold inducible promoter from TF55gamma and (c) a promoter inducible by a carbon source.

10. The expression vector of claim 1, wherein the vector contains an additional expression cassette for a reporter protein selected from the group consisting of a (β-galactosidase, a luciferase, a green fluorescent protein and variants thereof.

11. A shuttle vector comprising the sequences of the expression vector of claim 1 and additional sequences for propagation and selection in $E.\ coli$, wherein the additional sequences comprise
   (a) an $E.\ coli$ on of replication; and
   (b) a marker for selection in $E.\ coli$.

12. The shuttle vector of claim 11, wherein the marker for selection is selected from the group consisting of ampicillin, kanamycin, chloramphenicol, tetracyclin, hygromycin, neomycin or methotrexate.

13. A host cell transformed with the expression vector of claim 1, wherein the host cell is $E.\ coli$ or a sulfolobus cell.

14. The host cell of claim 13, wherein the transformed expression vector has a gene encoding a second essential protein.

15. The host cell of claim 13, wherein the host is deficient in expressing a fully functional version of said essential gene provided by the expression vector.

16. A method of producing a polypeptide encoded by the gene of interest, the method comprising culturing the host cell of claim 13 under suitable conditions and isolating said polypeptide from the cells or the cell culture supernatant.

17. A method of generating infectious recombinant subviral particles composed of the structural proteins of a SSV1 or a SSV2 virus and comprising the expression vector of claim 1, wherein the method has the steps of
   (a) introducing the expression vector and the SSV1 or the SSV2 DNA into a host cell;
   (b) incubating the cells under conditions sufficient to allow expression of the SSV1 or the SSV2 structural proteins and production of the infectious recombinant subviral particles; and
   (c) harvesting the infectious recombinant subviral particles.

18. The expression vector of claim 1, wherein the gene of interest is transcribed into an RNAi or antisense RNA.

19. A kit comprising
   (a) the vector of claim 1, or
   (b) the host cell of claim 13, and/or
   (c) a host cell deficient in the expression of the essential protein of the vector of (a)
   in one or more containers.

* * * * *